United States Patent [19]

Geist

[11] 4,333,468
[45] Jun. 8, 1982

[54] MESENTERY TUBE HOLDER APPARATUS

[76] Inventor: Robert W. Geist, 7 Sandpiper La., St. Paul, Minn. 55110

[21] Appl. No.: 178,912

[22] Filed: Aug. 18, 1980

[51] Int. Cl.³ .............................................. A61M 25/02
[52] U.S. Cl. ............................ 128/348; 128/DIG. 26
[58] Field of Search ............................... 128/348–350, 128/133, 214 R, DIG. 26

[56] References Cited

U.S. PATENT DOCUMENTS

| 3,677,250 | 7/1972 | Thomas | 128/348 |
|---|---|---|---|
| 3,826,254 | 7/1974 | Mellor | 128/133 |
| 3,834,380 | 9/1974 | Boyd | 128/133 |
| 4,165,748 | 8/1979 | Johnson | 128/348 |

Primary Examiner—Dalton L. Truluck
Attorney, Agent, or Firm—Clayton R. Johnson

[57] ABSTRACT

Mesentery tube apparatus that may be adhered to various portions of a patient's body for holding a tube such as a catheter and permits replacement of the tube while the apparatus is still adhered to the body, said apparatus including a base plate of sufficient flexibility to conform to the part of the human body to which it is to be adhered, a self adhesive coating on one surface of the plate for adhering the plate to the body and at least one flap having an end portion permanently adhered to the base plate. In one embodiment the base plate has an upwardly opening groove to have the tube extend thereinto and there is provided only one flap which has a self adhesive coating for adhering to the part of the tube extending radially outwardly of the groove and to adhere to a self adhesive coating on the base plate on either side of the groove, there being a self adhesive coating extending across the grooved portion. In the second embodiment there are provided two flaps having their remote end portions permanently adhered to the base plate and adjacent intermediate portions with permanent adhesive to adhere them to one another above the base plate, and self adhesive on portions above the said intermediate portions to adhere one to the other above the tube and to adhere to adjacent surfaces of the tube to support the tube in spaced relationship to the base plate.

14 Claims, 4 Drawing Figures

MESENTERY TUBE HOLDER APPARATUS

BACKGROUND OF THE INVENTION

This invention relates to apparatus for fastening a tube, for example a catheter, to a patient's body.

Medical personnel have a problem in taping urethral, abdominal, and chest drainage tubes to a patient's skin. If a tube is not taped to the skin, an accidental yank is directly transmitted to the urethra or skin stitches which causes patient discomfort. Rarely do medical personnel have the skill to make a proper mesentery using ordinary hospital self adhesive tape for holding a catheter or tube to the skin. When the personnel have sufficient skill, such ordinary tape does not work well since it is too pliable and pulls off the skin too easily.

In U.S. Pat. No. 3,826,254 there is disclosed a needle or catheter retaining appliance that includes a pad having a first section with a self adhesive layer for adhering to a patient's body and a second section adapted to be folded over the first section to hold a tube therebetween, the adjacent surfaces of the first and second sections each having a self adhesive layer.

U.S. Pat. No. 3,834,380 discloses a strip of tape having pressure sensitive adhesive and a slit clamping tube molded integral with the tape on the side opposite the adhesive. Latching means may be provided to retain items on the clamping tube. The latching means includes a latching flap adhesively secured to one side of the clamping tube to be folded thereover and having a pad to interlock with a pad attached to the tape.

U.S. Pat. Nos. 3,696,920 and 3,630,195 disclose grooved blocks for holding tubing, a layer of adhesive being provided for retaining the block on a patient.

In U.S. Pat. No. 4,165,748 there is disclosed a catheter tube holder made of a single piece having one side covered with a pressure sensitive adhesive and has a central bridge portion adapted to be wrapped around the tube with a nonadhesive surface abutting against the tube. Snaps or adhesive spots are provided to hold the bridge portion folded as shown in FIG. 2 of the patent, but permit separation of the spots so that the tube can be removed without removing the end portions of the holder from the patient's body.

SUMMARY OF THE INVENTION

Mesentery tube holder apparatus that includes a base plate of moderately pliable material that will contour to a patient's skin, a self adhesive coating on one surface of the base plate and at least one flap having one end portion permanently adhered to the opposite surface of the base plate and an opposite end portion having self adhesive thereon for adhering to the tube.

One of the objects of this invention is to provide new and novel means for holding a tube or catheter to a patient's skin. Another object of this invention is to provide new and novel means for adhering to a patient's body and holding a tube while permitting replacement of the tube without removal of the device from the skin. A further object of the invention is to provide new and novel means adherable to a patient's skin for holding and supporting a tube while permitting limited movement of the held part of the tube.

BRIEF DESCRIPTION OF THE DRAWINGS

Referring now to FIGS. 1 and 2, the first embodiment of the invention includes a generally rectangular, longitudinally elongated base plate 10, 12 that includes a lower portion 10 made of a moderately pliable material, for example plastic, that can be readily contoured to the skin of a patient's leg, abdomen, chest or etc. but of sufficient bulk and rigidity to prevent being dislodged by muscle flexing the skin surface or by accidental pulling. Thus, the base plate lower portion is of greater bulk and rigidity than the tape of bandages such as sold under the trademark Band Aids.

Figure 1:
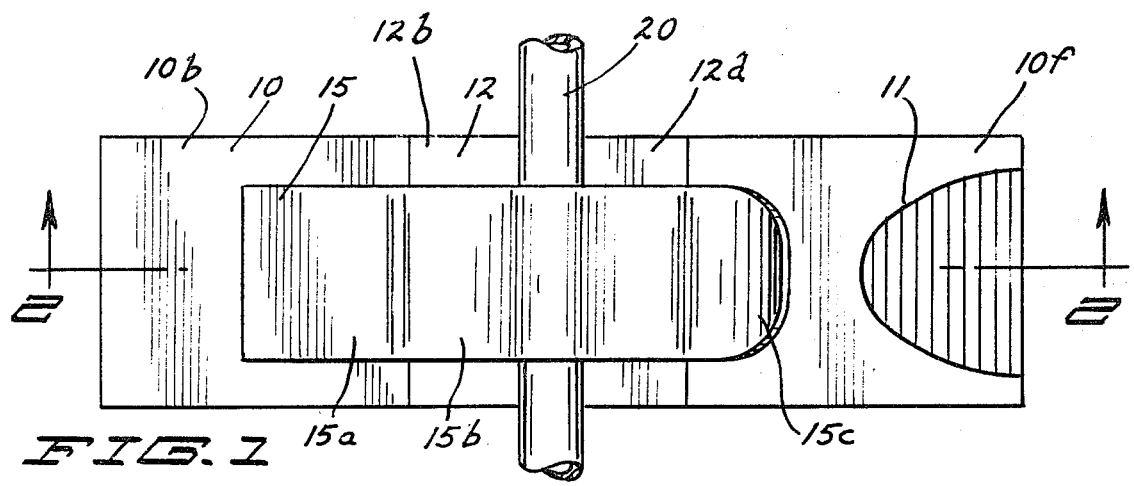
FIG. 1 is a plan view of the first embodiment of the invention in a flat condition holding a tube, said view being generally taken along the line and in the direction of the arrows 1—1 of FIG. 2.
Figure 2:
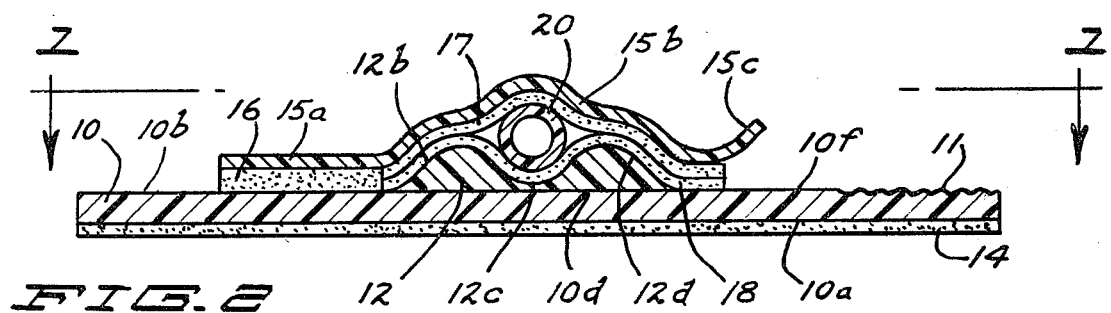
FIG. 2 is a longitudinal cross sectional view generally taken along the line and in the direction of the arrows 2—2 of FIG. 1.

In a flat condition the undersurface 10a of the base plate 10 is generally planar while the upper surface of portion 10 is generally planar and includes one end surface portion 10b, an intermediate surface portion 10d and an opposite end surface portion 10f which has a depression 11 that provides a thumb placement area. The undersurface 10a is covered with a layer 14 of pressure sensitive adhesive (self adhesive) suitable for adhering to a patient's skin.

The base plate upper portion 12 is preferably made of a soft, more pliable material than upper portion 10, so as to more readily contour to a tube 20. In a base plate flat condition, the upper portion has a lower surface permanently bonded to the surface portion 10d. From the end adjacent end portion 10b the upper portion 12 has an upper surface that is curved upwardly along 12b, thence downwardly and next upwardly to form a transverse groove 12c and thence curved downwardly along surface portion 12d to terminate adjacent end portion 10f. Thus, the thickness of the base plate at the uppermost parts of surface portions 12b, 12b is substantially greater than at the most recessed portion of groove 12c. Even though the upper portion is shown in FIG. 1 as being the same transverse width as the lower portion, it is to be understood the upper portion may be of the same transverse dimension as the intermediate portion 15b of flap 15 which will be referred to hereinafter. Preferably the groove would extend across the entire transverse width part of the upper portion even though the lower portion is of a greater transverse width than the upper portion 12. In any event, the groove would be of at least a transverse width to underlay the width of flap portion 15b when in a position for holding a tube.

Even though it is preferred that upper portion 12 be made of a softer material than lower portion 10, it is to be understood that portion 12 may be made of the same material as that of portion 10 and portions 10, 12 may be made from a single piece of material (integrally formed). Thus the base plate whether formed of two different types of material or an integrally formed member, has upper surface portions 10b, 12b, 12c, 12d, 10f.

There is provided a longitudinally elongated rectangular flap 15 that is of a substantially smaller length and transverse width than the corresponding dimensions of the base plate lower portion. The end portion 15a of the flap that overlaps surface portion 10b is permanently secured to base plate by a layer of permanent adhesive 16 (the thickness of the layers of adhesive being exaggerated in the drawing). Flap 15 has a longitudinally intermediate portion 15b that in a position of use overlays base plate portions 12b, 12c, 12d and the adjacent part of the base plate portion 10f, the portion 15b having a layer of pressure sensitive adhesive 17 covering its surface that is adjacent the base plate and the base plate upper surface having a layer 18 of pressure sensitive adhesive covering the base plate upper surface that underlays portion 15b. Thus layer 18 is substantially the same transverse width as that of the flap and extends longitudinally along surface base plate surface portions 12b, 12c, 12d and part of surface portion 10f. The flap has a tab end portion 15c opposite end portion 15a that has no adhesive thereon so as to provide a finger grip portion, there being no adhesive on the upper surface of the base plate beneath tab 15c when the flap is in its position of use. As may be noted in FIG. 1, in a position of use the tab 15c is longitudinally spaced from thumb placement area 11.

Preferably peel-off back strips (not shown) are provided to cover the entire undersurface area of adhesive layer 14, and between adhesive layers 17 and 18, which are to be peeled off just before use of the first embodiment.

After the end portion of tube 20 has been properly extended into a body opening (natural or surgically made) or a needle (not shown) on said end portion of the tube extends through a skin puncture, the peel-off strip, if any, covering adhesive 14 is removed and the first embodiment is properly positioned between the part of tube to be held and the patient's skin. Now tab 15c is lifted so that flap portion 15b hinges adjacent the juncture of flap portions 15a, 15b and the tube pressed downwardly to extend into the grooved portion of the base plate and be adhered thereto by the adjacent part of adhesive layer 18 that extends longitudinally across the groove surface portion. Then, with tab 15c under slight tension, the tab is moved toward base plate surface portion 10f and a finger or fingers moved along flap portion 15b so that the adjacent parts of the adhesive layers between surface portion 12b and flap portion 15b adhere to one another, the portion of layer 17 adheres to the adjacent part of the tube 20 opposite layer 18 and the adjacent parts of layers 17, 18 between flap portion 15b and surface portions 12b, 12c, 12d and 10f adhere to one another. Preferably the flap is made of a stretchy type of tape so that it will more readily contour to the tube and the softer base plate material 12.

The tube may be replaced without removal of the base plate from the patient's skin. The thumb replacement area 11 on the base plate would remind a person to hold down on the base plate while pulling up on tab 15c to fold back portion 15b over portion 15a. Thereafter the tube may be lifted up off adhesive layer 18, replacing with another tube, and tab 15c moved to secure the tube to the base plate as previously described.

Figure 3:
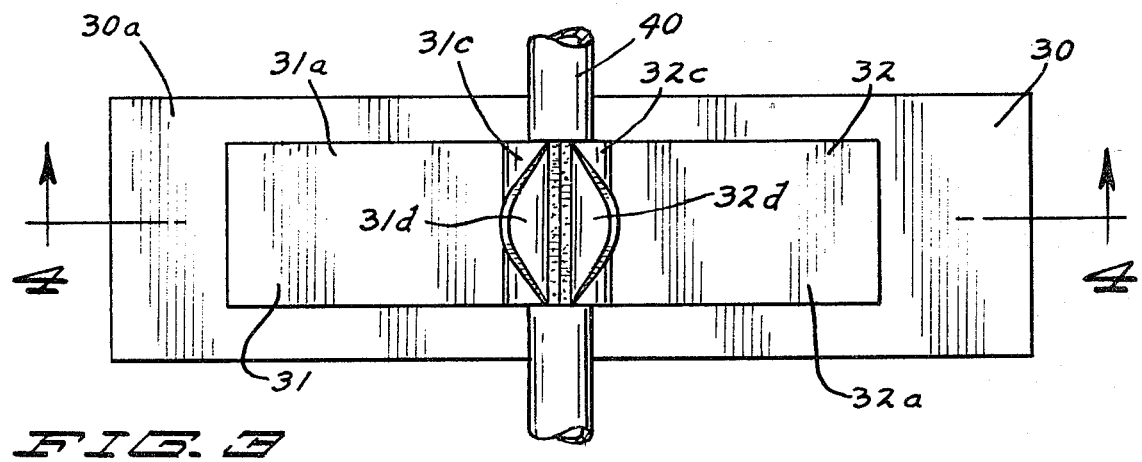
FIG. 3 is a plan view of the second embodiment of the invention in a flat condition holding a tube, said view being generally taken along the line and in the direction of the arrows 3—3 of FIG. 4.
Figure 4:
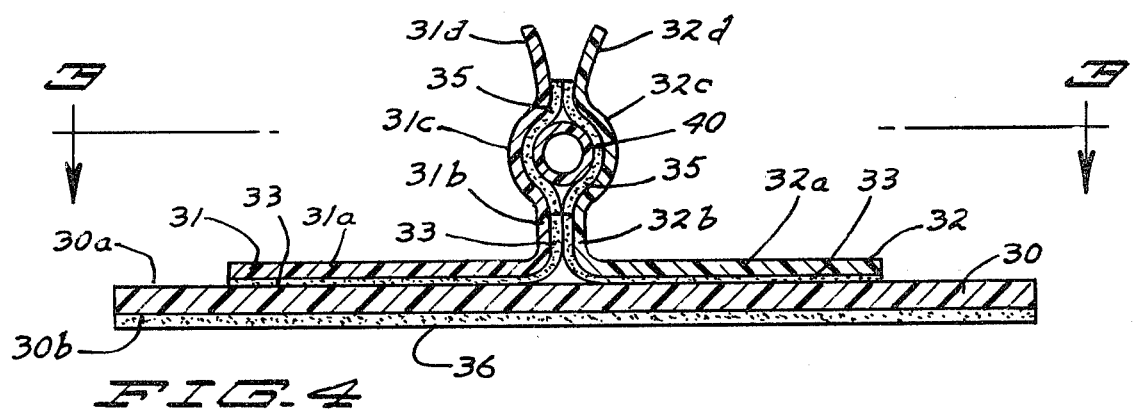
FIG. 4 is a longitudinal cross sectional view generally taken along the line and in the direction of the arrows 4—4 of FIG. 3.

Referring now to FIGS. 3 and 4, the second embodiment of the invention includes a longitudinally elongated generally rectangular base plate 30 made of the same material as plate 10, but in a flat condition has generally planar upper and lower surfaces 30a and 30b respectively. The lower surface is curved with a layer of pressure sensitive adhesive 36 that is adhered thereto.

A pair of generally rectangular flaps 31, 32 which advantageously may be of the same size and shape, in a position the base plate is flat have generally planar, remote end portions 31a, 32a respectively secured to the base plate upper surface 30a by layers of permanent adhesive 33, and adjacent upwardly extending intermediate portions 31b, 32b likewise joined by the permanent adhesive 33. Intermediate portions 31b, 32b are integrally joined to portions 31a, 32a respectively, and extend above portions 31a, 32a, for example on ¼" or higher, depending on the outer diameter of tube the second embodiment is to be used with and the type of usage. The intermediate portions 31c, 32c have one ends integrally joined to portions 31b, 32b respectively to extend away therefrom and on their adjacent surfaces there is provided a layer of pressure sensitive adhesive 35. The opposite end portions 31d, 32d are integrally joined to portions 31c, 32c respectively, do not have any adhesive thereon and serve as pull tabs. Advantageously, a peel-off strip (not shown) may be provided to cover the undersurface of adhesive layer 36 and a pull-off strip provided between the adhesive layers 35 on flap portions 31c, 32c.

To use the second embodiment the peel-off strip, if any, is separated from adhesive layer 36 and then the adhesive layer 36 adhered to the patient's skin in the desired position. Now the tabs 31d, 32d are pulled apart, the peel-off strip, if any, is separated from adhesive layers 35 and flap portions 31c, 32c are molded around the tube 40 with finger pressure. Thus the layer of adhesive 35 on flap portion 31c adheres to one side of the tube and the adhesive layer 35 on flap portion 32c adheres to the opposite side of the tube while the tube bottom is located closely adjacent the juncture of portions 31c, 32c, to portions 31b, 32b. Portions 31c, 32c that have adhesive 35 thereon are of sufficient lengths that the parts adhesive layers 35 above the tube can be pressed together to adhere to one another.

When it is desired to remove tube 40 the pull tabs can be pulled apart to separate the layers of adhesive 35 above the tube and the tube removed while adhesive 36 remains adhered to the patient's skin. Another tube can be held in place by the flaps by following the procedure set forth above.

The flaps 31, 32 are made of flexible tape and due to the flexibility thereof and of the adhesive used, portions 31b, 32b may be bent about transverse axes parallel to the upper surface of the base plate and twisted a limited amount about axes generally perpendicular thereof. The length of portions 31b, 32b would in part depend on the usage. For example, if the base plate 40 is to be adhered to the bridge of the nose to hold a nasogastric tube, portions 31b, 32b advantageously would be of substantially greater lengths (for example to reach down past the tip of the nose so that flap portions 31c, 32c encircled the tube as it came out of a nostril) then when, for example, being used affixed a tube to the abdomen.

The base plates may be made in varying lengths and widths, the sizes and shapes in part depending on the diameter of tube and in part on the part of the body, for example thigh, abdomen or chest, that the tube is to be affixed to.

What is claimed is:

1. Apparatus for affixing a medical tube or the like to a body comprising a base plate contourable to the shape of a part of the body and in a flat condition having an upper surface and a lower surface, said upper surface including a first end portion, an intermediate surface portion, and an opposite end surface portion, the base plate intermediate portion having an upwardly opening transverse groove, the thickness of the base plate longitudinally on either side of the groove being substantially greater than the thickness of either of the base plate end portions, a layer of pressure sensitive adhesive covering the lower surface for adhering the base plate to the body, and means for affixing a tube to the base plate, said means including an elongated first flap having a first end portion, an intermediate portion and an opposite end portion, a layer of permanent adhesive for bonding the flap first end portion to the base plate first end portion and pressure sensitive adhesive for adhering the flap intermediate portion to the tube and to the base plate intermediate portion longitudinally on either side of the groove that is of a substantially greater thickness than the base plate end portions.

2. The apparatus of claim 1 further characterized in that the flap opposite end portion is free of adhesive to provide a pull tab.

3. The apparatus of claim 1 further characterized in that the base plate is of a substantially greater bulk and rigidity than the flap.

4. Apparatus for affixing a medical tube or the like to a body comprising a base plate contourable to the shape of a part of the body and in a flat condition having an upper surface and a lower surface, said upper surface including a first end portion, an intermediate surface portion and an opposite end surface portion, the base plate intermediate portion having an upwardly opening transverse groove, the thickness of the base plate longitudinally on either side of the groove being substantially greater than the thickness of either of the base plate end portions, a layer of pressure sensitive adhesive covering the lower surface for adhering the base plate to the body, and means for affixing a tube to the base plate, said means including an elongated first flap having a first end portion, an intermediate end portion, and an opposite end portion, a layer of permanent adhesive for bonding the flap first end portion to the base plate first end portion, a layer of pressure sensitive adhesive on the flap intermediate portion for adhering to the tube, and a layer of pressure sensitive adhesive on the base plate upper surface extending longitudinally across the groove.

5. Apparatus for affixing a medical tube or the like to a body comprising a base plate contourable to the shape of a part of the body and in a flat condition having an upper surface and a lower surface, said upper surface including a first end portion, an intermediate surface portion and an opposite end surface portion, a layer of pressure sensitive adhesive covering the lower surface for adhering the base plate to the body, and means for affixing a tube to the base plate, said means including an elongated first flap having a first end portion, an intermediate end portion, and an opposite end portion, a layer of permanent adhesive for bonding the first flap end portion to the base plate first end portion, an elongated second flap having a first end portion, an intermediate portion and an opposite end portion, a layer of permanent adhesive for bonding the second flap first end portion to the base opposite end portion with the flaps intermediate portions adjacent and extending away from the base plate and adhesive means for adhering the flaps intermediate portions to one another for holding a tube therebetween, including more closely adjacent the base plate along the length of the flaps intermediate portions than a tube and more remote from the base plate along the length of the flaps intermediate portions than the tube.

6. The apparatus of claim 5 further characterized in that the adhesive means includes pressure sensitive adhesive on the flap intermediate portions for adhering to a tube.

7. The apparatus of claim 5 further characterized in that the adhesive means comprises a pressure sensitive adhesive layer on each flap intermediate portion for adhering to each other along the length of the flap intermediate portions more remote from the base plate than a tube and on the second flap intermediate portion for adherence to the tube.

8. The apparatus of claim 7 further characterized in that the adhesive means comprises a layer of permanent adhesive for bonding the flap intermediate portions to one another along the length thereof from adjacent the base plate to adjacent the adhesive for adherence to a tube.

9. The apparatus of claim 7 further characterized in that each of the flaps is of about the same length, that the flaps first end portions and intermediate portions are respectively of about the same lengths and that the flap opposite end portions are free of adhesive to provide pull tabs.

10. Apparatus for affixing a medical tube to a part of a patient's body comprising a base plate contourable to the shape of a part of the body and having an upper surface and a lower surface, said upper surface including a first end surface portion and a second end surface portion, a first and a second elongated flap that along the length thereof each have a first end portion extending remote from the other, a first intermediate portion adjacent the first intermediate portion of the other and joined to the respective flap first end portion, a second intermediate portion joined to the respective flap first intermediate portion, and a third intermediate portion joined to the respective flap second intermediate portion and a second end portion joined to the respective flap third intermediate portion, first means for attaching the first flap first end portion to the base plate first end portion, second means for attaching the second flap first end portion to the base plate second end portion, third means for joining the flap first intermediate portions to one another and means for releasably joining the flaps third intermediate portions to one another with a tube extended between the flaps second intermediate portions, and a pressure sensitive layer covering the undersurface for adhering the plate to a part of a body.

11. The apparatus of claim 10 further characterized in that the last mentioned means comprises pressure sensitive adhesive.

12. The apparatus of claim 10 further characterized in that the flaps second intermediate portions have adjacent surfaces and that there is provided pressure sensitive adhesive on each of the adjacent surfaces of the flaps second intermediate portions for adherence to a tube.

13. The apparatus of claim 10 further characterized in that each of the first and second means comprises a permanent adhesive and that each flap second end portion is free of adhesive to provide a pull tab.

14. The apparatus of claim 13 further characterized in that each of the third means comprises pressure sensitive adhesive.

* * * * *